(12) United States Patent
Choi

(10) Patent No.: US 10,638,984 B2
(45) Date of Patent: May 5, 2020

(54) X-RAY COLLIMATOR AND X-RAY IMAGING APPARATUS USING SAME

(71) Applicants: VATECH Co., Ltd., Gyeonggi-do (KR); VATECH EWOO Holdings Co., Ltd., Gyeonggi-do (KR)

(72) Inventor: Sung Il Choi, Gyeonggi-do (KR)

(73) Assignees: VATECH Co., Ltd., Gyeonggi-do (KR); VATECH EWOO Holdings Co., Ltd., Gyeonggi-do (KR)

(*) Notice: Subject to any disclaimer, the term of this patent is extended or adjusted under 35 U.S.C. 154(b) by 0 days.

(21) Appl. No.: 16/075,751

(22) PCT Filed: Feb. 6, 2017

(86) PCT No.: PCT/KR2017/001274
§ 371 (c)(1),
(2) Date: Aug. 6, 2018

(87) PCT Pub. No.: WO2017/135782
PCT Pub. Date: Aug. 10, 2017

(65) Prior Publication Data
US 2019/0029614 A1 Jan. 31, 2019

(30) Foreign Application Priority Data
Feb. 5, 2016 (KR) .................. 10-2016-0014976

(51) Int. Cl.
*A61B 6/06* (2006.01)
*G21K 1/02* (2006.01)
(Continued)

(52) U.S. Cl.
CPC .............. *A61B 6/06* (2013.01); *A61B 6/032* (2013.01); *A61B 6/107* (2013.01); *A61B 6/547* (2013.01);
(Continued)

(58) Field of Classification Search
CPC .............. A61B 6/06; G21K 1/02; G21K 1/04
See application file for complete search history.

(56) References Cited

U.S. PATENT DOCUMENTS

| 4,534,052 A | 8/1985 | Milcamps |
| 5,012,506 A | 4/1991 | Span et al. |

(Continued)

FOREIGN PATENT DOCUMENTS

| DE | 10 2013 222 209 A1 | 4/2015 |
| JP | 2004-357956 A | 12/2004 |

(Continued)

OTHER PUBLICATIONS

European Patent Office, European Search Report of corresponding EP Patent Application No. 17747825.2, dated Jul. 9, 2019.

*Primary Examiner* — Thomas R Artman
(74) *Attorney, Agent, or Firm* — IP Legal Services, LLC

(57) ABSTRACT

The present invention relates to an X-ray collimator capable of adjusting a field of view during X-ray imaging and an X-ray imaging apparatus using the same, the apparatus including an X-ray light source configured to emit X-rays, an X-ray detector configured to detect the X-rays, and a collimator configured to provide an opening to determine an FOV of the X-rays between the X-ray light source and the X-ray detector, wherein the opening is configured such that at least one of a first edge at an entrance side facing the X-ray light source, and a second edge at an exit side facing the X-ray detector is formed in a curved shape.

7 Claims, 7 Drawing Sheets

(51) Int. Cl.
*G21K 1/04* (2006.01)
*A61B 6/03* (2006.01)
*A61B 6/10* (2006.01)
*A61B 6/00* (2006.01)

(52) U.S. Cl.
CPC .................. *A61B 6/58* (2013.01); *G21K 1/02* (2013.01); *G21K 1/046* (2013.01)

(56) References Cited

U.S. PATENT DOCUMENTS

| | | | |
|---|---|---|---|
| 5,165,106 A * | 11/1992 | Barthelmes | G21K 1/046 250/505.1 |
| 6,320,929 B1 | 11/2001 | Von Der Haar | |
| 2007/0003005 A1 | 1/2007 | Matsuda | |
| 2008/0063147 A1 | 3/2008 | Juschka et al. | |
| 2012/0051499 A1 | 3/2012 | Lee et al. | |
| 2014/0146948 A1 | 5/2014 | Zhang et al. | |
| 2015/0078508 A1 | 3/2015 | Lee et al. | |
| 2015/0131781 A1* | 5/2015 | Ohashi | A61B 6/542 378/62 |
| 2019/0029614 A1* | 1/2019 | Choi | A61B 6/06 |

FOREIGN PATENT DOCUMENTS

| | | |
|---|---|---|
| JP | 2007-037994 A | 2/2007 |
| KR | 10-1534098 B1 | 7/2015 |

* cited by examiner

X-RAY COLLIMATOR AND X-RAY IMAGING APPARATUS USING SAME

CROSS REFERENCE TO RELATED APPLICATIONS

This application is a National Stage Patent Application of PCT International Patent Application No. PCT/KR2017/001274 (filed on Feb. 6, 2017) under 35 U.S.C. § 371, which claims priority to Korean Patent Application No. 10-2016-0014976 (filed on Feb. 5, 2016), the teachings of which are incorporated herein in their entireties by reference.

TECHNICAL FIELD

The present invention relates generally to an X-ray collimator and an X-ray imaging apparatus using the same. More particularly, the present invention relates to an X-ray collimator capable of adjusting a field of view (FOV) during X-ray imaging and an X-ray imaging apparatus using the same.

BACKGROUND ART

In general, medical professionals, such as orthopedists or dentists use an X-ray imaging apparatus for diagnostic or therapeutic methods. In recent years, due to the development of digital X-ray imaging technology including a digital X-ray detector, X-ray imaging apparatuses that can be used for various purposes have been developed.

In particular, in the case of a dental X-ray imaging apparatus, a panoramic image, a computed tomographic image, and a cephalometric image can be imaged using a single apparatus. Thus, in order to obtain various types of X-ray images, it is necessary to adjust a field of view (FOV), that is, an area where X-rays are irradiated from an X-ray light source according to an X-ray image corresponding to the imaging purpose.

As described above, in the X-ray imaging apparatus, an X-ray collimator is a device for adjusting the FOV of the X-rays emitted from an X-ray light source. In a conventional X-ray collimator, a pair of metal plates arranged in parallel to each other is arranged in the X-axis direction and the Y-axis direction, respectively, and the gap between each pair of metal plates is adjusted so that an opening therebetween, i.e., the size of the opening through which X-rays can be irradiated, is adjusted.

FIG. 1 is a view showing a conventional X-ray collimator and an X-ray imaging apparatus using the same, and the conventional X-ray imaging apparatus includes an X-ray light source 10, a collimator 20 configured to an FOV of the X-rays emitted from the X-ray light source 10, and a detector 30 configured to detect the X-rays emitted from the X-ray light source 10.

However, the conventional X-ray collimator and the X-ray imaging apparatus using the same shown in FIG. 1 are configured such that edges of the opening of the collimator are in a vertically angled shape, wherein a part of the X-rays radially irradiated from the X-ray light source 10 is interfered or partially blocked at the angled edge portion, and a penumbra A is broadly generated at the edge portion of the image obtained at the detector 30.

Accordingly, the quality of the X-ray image is likely to be deteriorated, and if the penumbra A is removed from the X-ray image, the area of the detector 30 cannot be utilized sufficiently.

[Documents of Related Art] Korean Patent No. 10-1534098

DISCLOSURE

Technical Problem

Accordingly, the present invention has been made keeping in mind the above problems occurring in the related art, and one object of the present invention is to provide an X-ray collimator and an X-ray imaging apparatus using the same, in which the shape of edge portions of an opening of the collimator configured to adjust a field of view is changed from a conventional angled shape to a curved shape, such that the effect of unnecessary interference or partially blocking of X-rays, that is, a penumbra in an X-ray image, is reduced, whereby it is possible to improve the quality of the X-ray image and is possible to precisely control the X-ray imaging apparatus.

Technical Solution

In order to achieve the above object, according to some aspects of the present invention, there is provided an X-ray imaging apparatus including: an X-ray light source configured to emit X-rays; an X-ray detector configured to detect the X-rays; and a collimator configured to provide an opening to determine an FOV of the X-rays between the X-ray light source and the X-ray detector, wherein the opening includes at least one of a first edge at an entrance side facing the X-ray light source, and a second edge at an exit side facing the X-ray detector being formed in a curved shape.

Herein, the X-ray light source and the collimator may be arranged in a fixed relative position, and the first edge may be in a vertically angled shape and the second edge may be in the curved shape.

Further, the X-ray detector and the collimator may be moved with respect to each other in one direction, a first side edge of the opening facing the moving direction may be configured to be in a vertically angled shape at the first edge and in a curved shape at the second edge, and a second side edge of the opening may be configured to be in the curved shape at both the first edge and the second edge.

Meanwhile, the X-ray detector and the collimator may be moved with respect to each other in opposite directions, and the opening may include the first edge and the second edge are in the curved shape.

Further, the curved shape may be an arc shape.

Meanwhile, the curved shape may be an arc tangent to a line connecting the X-ray light source and a point of a part where intensity of the X-rays detected by the X-ray detector is 40% or more and 60% or less, assuming that the first edge and the second edge are in an angled shape.

Further, a radius of curvature of the arc may be equal to or less than a thickness of the collimator and equal to or more than half of the thickness of the collimator.

Meanwhile, according to some aspects of the present invention, there is provided an X-ray collimator configure to provide an opening to determine an FOV of X-rays between an X-ray light source configured to emit the X-rays and an X-ray detector configured to detect the X-rays, wherein when the X-ray light source and the collimator are arranged in a fixed relative position, the opening includes a first edge facing the X-ray light source being in an angled shape and a second edge facing the X-ray detector being in a curved shape; when the X-ray detector and the collimator are moved with respect to each other in one direction, a first side edge of the opening facing the moving direction is configured to be in an angled shape at the first edge and in a curved shape at the second edge, and a second side edge of the opening is configured to be in the curved shape at both the first edge and the second edge; and when the X-ray detector and the collimator are moved with respect to each other in opposite directions, the opening includes the first edge and the second edge being in the curved shape.

Further, the curved shape may be an arc shape.

Meanwhile, the curved shape may be an arc tangent to a line connecting the X-ray light source and a point of a part where intensity of the X-rays detected by the X-ray detector is 40% or more and 60% or less, assuming that both the first edge and the second edge are in an angled shape.

Advantageous Effects

According to the present invention, since the shape of edge portions of an opening of the collimator configured to adjust a field of view is changed from a conventional angled shape to a curved shape, the effect of unnecessary interference or partially blocking of X-rays, that is, a penumbra in an X-ray image, is reduced, whereby it is possible to improve the quality of the X-ray image and is possible to precisely control the X-ray imaging apparatus.

DESCRIPTION OF REFERENCE CHARACTERS OF IMPORTANT PARTS

Figure 1:
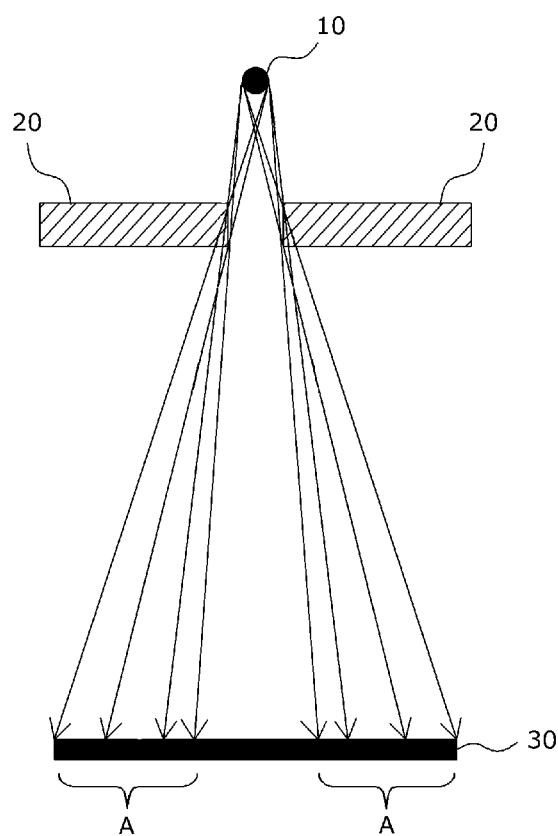
FIG. 1 is a view showing a conventional X-ray collimator and an X-ray imaging apparatus using the same.

100: X-ray light source
200: collimator
300: X-ray detector
400: driving unit cl MODE FOR INVENTION Hereinafter, various embodiments of the present invention will be described with reference to the accompanying drawings. The technical idea of the present invention will be understood more clearly by the embodiments. The present invention is not limited to the embodiments described hereinbelow. The same reference numerals are used to designate the same or similar components, and a description of components having the same reference numerals as those described in any one of the drawings may be omitted.

Figure 2:
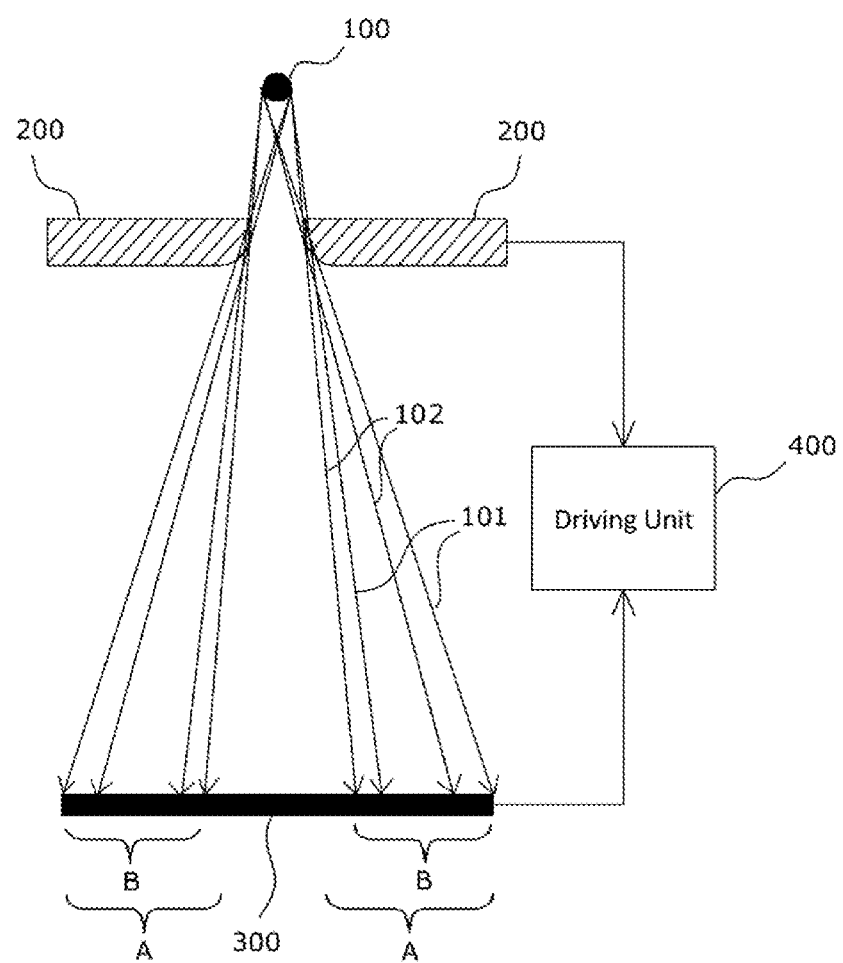
FIG. 2 is a view showing an X-ray collimator and an X-ray imaging apparatus using the same according to an embodiment of the present invention.
Figure 3A:
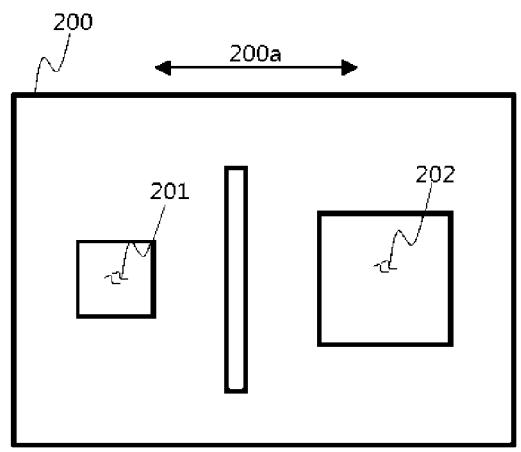
FIGS. 3a and 3b are views showing various structures of the X-ray collimator according to an embodiment of the present invention.
Figure 3B:
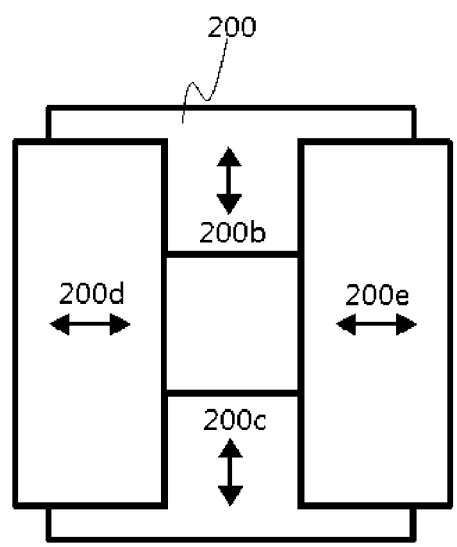

FIG. 2 is a view showing an X-ray collimator and an X-ray imaging apparatus using the same according to an embodiment of the present invention, and FIGS. 3a and 3b are views showing various structures of the X-ray collimator according to an embodiment of the present invention, wherein an X-ray imaging apparatus according to an embodiment of the present invention may include an X-ray light source 100, a collimator 200, an X-ray detector 300, and a driving unit 400.

The X-ray light source 100 radially emits X-rays in the direction of the X-ray detector 300. Herein, a subject is disposed between the X-ray light source 100 and the X-ray detector 300.

The collimator 200 collimates an FOV of the X-rays emitted from the X-ray light source 100. To achieve this, the collimator 200 provides an opening to determine an FOV of the X-rays between the X-ray light source 100 and the X-ray detector 300, and the driving unit 400 adjusts the size and shape of the opening. Here, the collimator 200 may include at least one X-ray shielding metal plate, and the driving unit 400 may be configured to adjust the size and shape of the opening by moving the at least one X-ray shielding metal plate.

Herein, the shielding metal plate of the collimator 200 is formed of a metal material that blocks X-rays, at least one of which is placed on the irradiation path of X-rays to provide an opening through which X-rays pass, and particularly, at least a part of the edge portion of the opening has a curved cross-section perpendicular to the longitudinal direction. In other words, by changing the cross-section perpendicular to the longitudinal direction of at least a part of the edge portion of the opening of the collimator 200 from a conventional angled shape to a curved shape, it is possible to reduce the effect of unnecessary interference or partially blocking of X-rays, that is, a penumbra in an X-ray image. Here, the curved shape may be, for example, an arc shape having a predetermined curvature.

Herein, assuming that the X-ray imaging apparatus is for at least one of a dental panoramic image, a tomographic image, and a cephalometric image, and the material of the shielding metal plate of the collimator 200 is lead (Pb), the thickness of the shielding metal plate of the collimator 200 should be at least 2 mm to 3 mm to show the shielding effect from X-rays.

Further, when the collimator 200 is arranged in a fixed position with respect to the X-ray light source 100, of the edges of the opening of the collimator 200, a part facing the X-ray light source 100 does not greatly affect the penumbra of the X-ray image, so the angular shape can be maintained as shown in FIG. 2, and of the edges of the opening of the collimator 200, a part facing the X-ray detector 300 may be a curved shape having a predetermined curvature. In other words, of the edges of the opening of the collimator 200, a first edge facing the X-ray light source may maintain an angular shape, and of the edges of the opening of the collimator 200, a second edge facing the X-ray detector 300 may be a curved shape having a predetermined curvature.

To be more specific, X-rays emitted from the X-ray light source 100 show the radial travel path. Thus, when the collimator 200 is arranged in a fixed position with respect to the X-ray light source 100, of the edges of the opening of the collimator 200, X-rays irradiated onto the first edge facing the X-ray light source 100 are more likely to be blocked by the collimator. On the contrary, of the edges of the opening of the collimator 200, X-rays irradiated onto the second edge facing the X-ray detector 300 are not blocked, and some of them are likely to penetrate or cause interference.

Accordingly, assuming that the collimator 200 is arranged in a fixed position with respect to the X-ray light source 100, the collimator 200 according to the present invention is configured such that of the edges of the opening, the second edge facing the X-ray detector 300 is formed in a predetermined curved shape.

Meanwhile, the collimator 200 according to the present invention configured such that a part of the edges of the opening is formed in a predetermined curved shape is applicable to various collimators.

For example, as shown in FIG. 3a, the collimator according to the present invention may include at least one shielding metal plate, and the at least one shielding metal plate may be formed with through holes 201 and 202 having different sizes and shapes to provide respective openings. In this case, by moving the at least one shielding metal plate appropriately by using the driving unit 400 shown in FIG. 2, an opening of a through hole having a desired size and shape can be arranged to correspond to the X-ray light source, and here, the present invention can be applied to the so-called window-type collimator to make the edge portion of the opening curved.

In other words, the collimator 200 according to the present invention is configured such that at least one shielding metal plate is moved according to the control of the driving unit 400 to provide any one of the through holes 201 and 202 having different sizes and shapes as an opening, and the curved structure is applied to the edge portion of the through hole of the collimator 200, i.e., the opening, whereby it is possible to reduce the penumbra in the X-ray image.

Meanwhile, as shown in FIG. 3b, the collimator according to the present invention is provided with two pairs of blades parallel to each other, as shielding metal plates, and with the two pairs of blades crossing each other, a gap between at least one pair of blades is adjusted by the control of the driving unit, whereby the size and shape of the opening formed therebetween can be adjusted. The present invention can be applied to a collimator of this type, a so-called blade type collimator, so that the edge portion of the opening can be formed in a curved structure.

In other words, the collimator according to the present invention is configured such that as four blades are moved according to the control of the driving unit 400, the size and shape of the opening is adjusted, and the edge portion of the opening of the collimator is applied with a curved structure, whereby it is possible to reduce the penumbra in the X-ray image.

Meanwhile, the X-ray detector 300 detects the X-rays being irradiated through the opening of the collimator 200 and penetrating through the subject, and transmits the detected result to an image data processing unit (not shown). In other words, the X-ray detector 300 acquires frame data transmitted through the subject at a preset frame rate, and the image data processing unit acquires an X-ray image based on the frame data received from the X-ray detector 300.

Here, a part of the X-rays radially irradiated from the X-ray light source 100 penetrates through the edge portion of the opening of the collimator 200, and this causes the X-ray detector 300 to detect X-rays that are not completely blocked by the collimator 200, that is, X-rays with relatively weak intensity compared to the initial X-rays in the area between an X-ray path 101 that reaches the X-ray detector 300 through the edge of the opening at the maximum length and an X-ray path 102 that reaches the X-ray detector 300 through the edge of the opening at the minimum length.

Further, a penumbra B is shown in the X-ray image due to the influence of the X-rays, the X-ray collimator and the X-ray imaging apparatus using the same according to the present invention is configured such that the edge portion of the opening of the collimator 200 is formed in a curved shape, thereby reducing the area of the penumbra B compared to the conventional X-ray collimator and an X-ray imaging apparatus using the same.

Figure 4A:
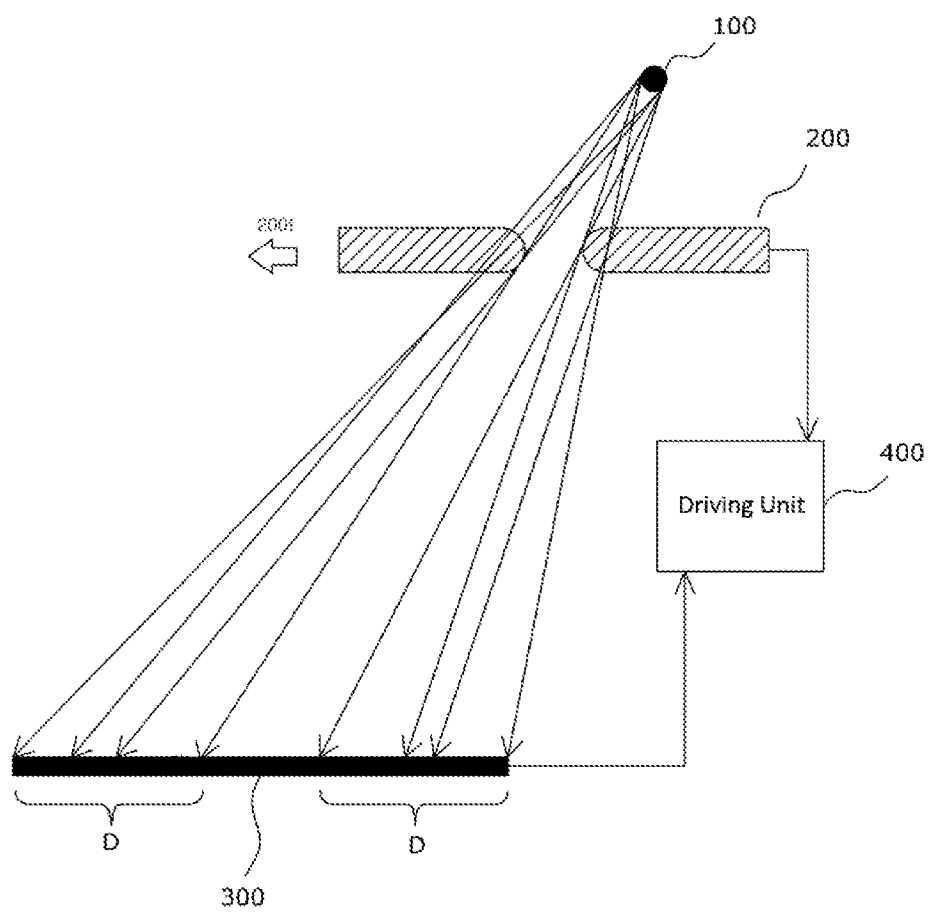
FIGS. 4a and 4b are views showing an X-ray collimator and an X-ray imaging apparatus using the same according to another embodiment of the present invention.
Figure 4B:
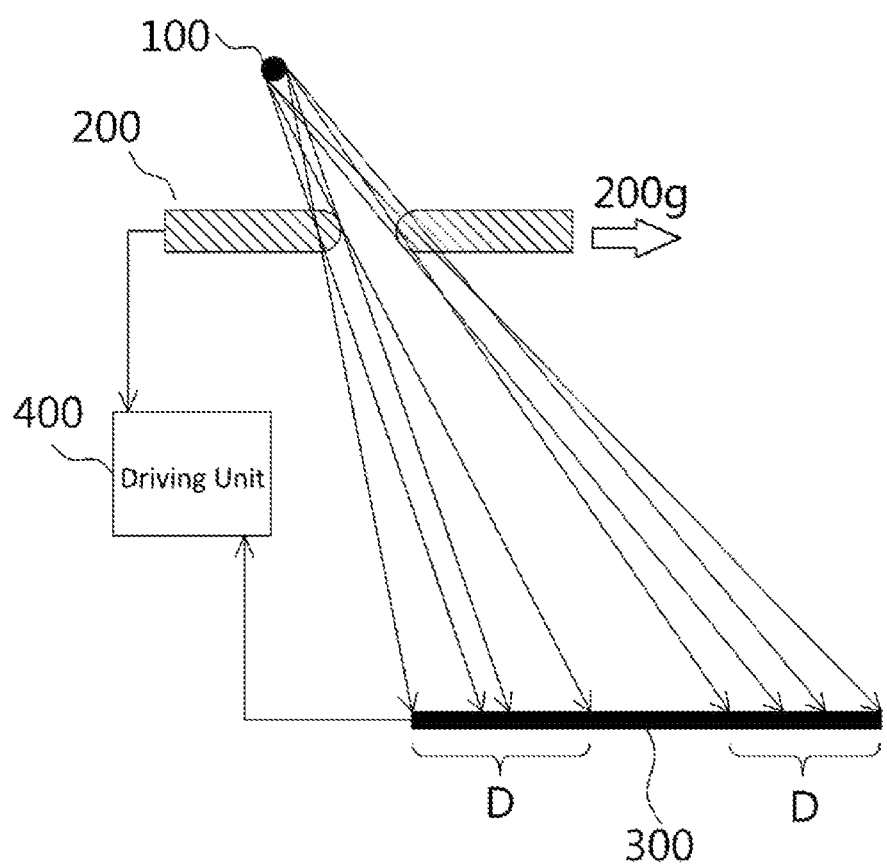

FIGS. 4a and 4b are views showing an X-ray collimator and an X-ray imaging apparatus using the same according to another embodiment of the present invention, wherein the driving unit 400 can adjust the relative positions of the X-ray light source 100 and the collimator 200 in addition to adjusting the shape and size of the opening of the collimator 200.

Here, the X-ray light source 100 irradiates X-rays in the direction of the X-ray detector 300 through the opening of the collimator 200, and when the collimator 200 is moved with respect to the X-ray light source 100, X-rays penetrating through the opening of the collimator 200 are also scanned to the X-ray detector 300 along the corresponding direction. In other words, the collimator 200 can be moved with respect to the X-ray light source 100 by the control of the driving unit 400, and through this, the direction of the X-ray irradiation path can be adjusted to perform the scan mode in which X-rays are scanned onto the X-ray detector 300.

As described, when the position of the collimator 200 with respect to the X-ray light source 100 is changed, of the edges of the opening of the collimator 200, the first edge facing the X-ray light source 100 influences the penumbra in the X-ray image, and thus as shown in FIGS. 4a and 4b, of the edges of the opening of the collimator 200, both the first edge facing the X-ray light source 100 and the second edge facing the X-ray detector 300 may be formed to have a curved structure, and as a result, the edge of the opening may be in a semi-circular shape or similar thereto.

Here, when the collimator 200 is moved only in one direction while the X-ray light source 100 irradiates X-rays, a first side edge of the opening facing the direction of movement may be configured such that as shown in FIG. 2, the second edge corresponding to the X-ray detector 300 side is formed in a curved shape, and a second side edge of the opening may be configured such that both the first and second edges are in a semi-circular shape or similar thereto.

For example, as shown in FIG. 4a, when the collimator 200 is moved with respect to the X-ray light source 100 only in one direction 200f while the X-ray light source 100 irradiates X-rays, the first side edge of the opening of the collimator 200 facing the direction of movement may be configured such that the second edge facing the X-ray detector 200 is in a curved shape, and the second side edge may be configured such that both the first and second edges are in a curved semi-circular shape, i.e., an arc shape.

On the contrary, when the collimator 200 is movable with respect to the X-ray light source 100 in opposite directions, i.e., the direction 200f shown in FIG. 4a, and another direction 200g shown in FIG. 4b, opposite portions of the opening of the collimator 200 may be configured such that both the first and second edges are in a curved semi-circular shape.

Meanwhile, although in the above description, the area of the X-ray detector 300 is relatively large, so that X-rays are scanned on a part of the X-ray detector 300 according to the relative movement of the X-ray light source 100 and the collimator 200, if necessary, the X-ray detector 300 may represent a small area corresponding to the X-rays transmitted through the collimator 200, and simultaneously, may detect X-rays while moving along the scan direction of X-rays according to the relative positional movement of the X-ray light source 100 and the collimator 200 under the control of the driving unit 400.

Here, the driving unit 400 may move all of the X-ray light source 100, the collimator 200, and the X-ray detector 300, and in this case, the driving unit 400 moves the X-ray light source 100, the collimator 200, and the X-ray detector 300 in synchronization with each other so that X-rays transmitted through the opening of the collimator 200 can be detected by the X-ray detector 300. For example, when the distance between the X-ray light source 100 and the collimator 200 is relatively short, even if the opening of the collimator 200 is slightly moved, the irradiation path of the X-rays may be moved relatively a lot along the moving direction of the opening, so the X-ray detector 300 is moved to correspond thereto. On the contrary, when the distance between the X-ray light source 100 and the collimator 200 is long, even if the opening of the collimator 200 is moved a lot, the irradiation path of the X-rays is moved slightly along the moving direction of the opening, so the X-ray detector 300 is moved to correspond thereto.

Figure 5:
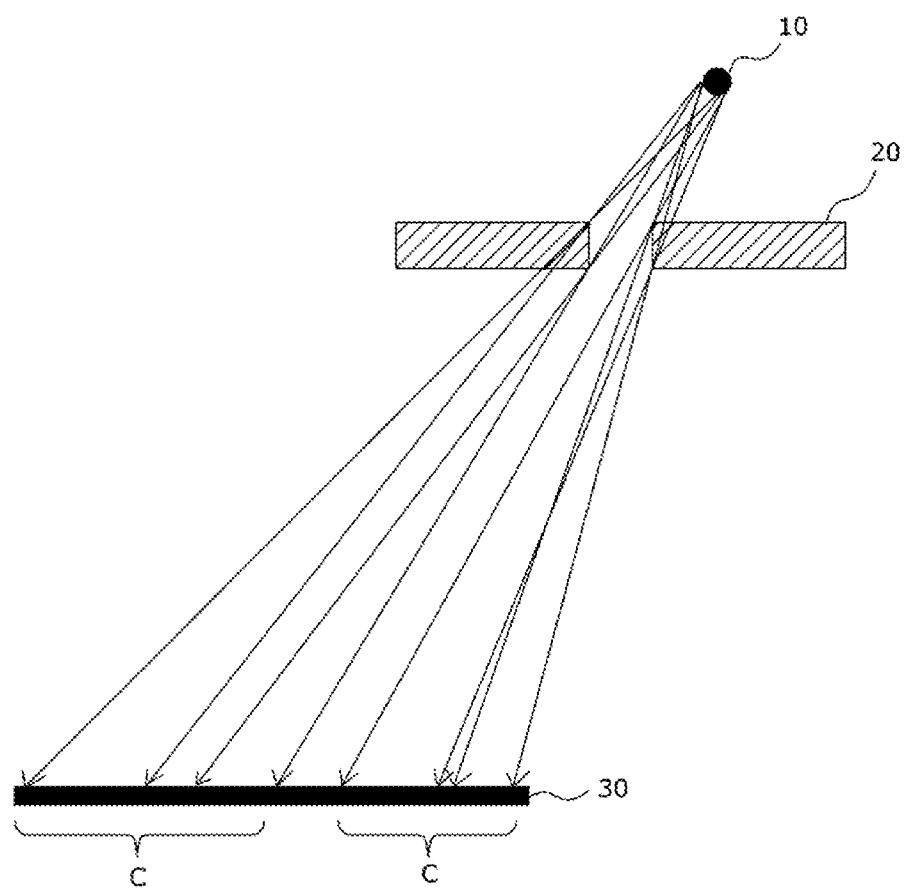
FIG. 5 is a view showing the conventional X-ray collimator and the X-ray imaging apparatus using the same providing a scan mode.

As shown in FIGS. 4*a* and 4*b*, in the case of the X-ray collimator and the X-ray imaging apparatus using the same according to the present invention, a penumbra D is reduced compared to a conventional angled collimator 20 shown in FIG. 5.

Figure 6:
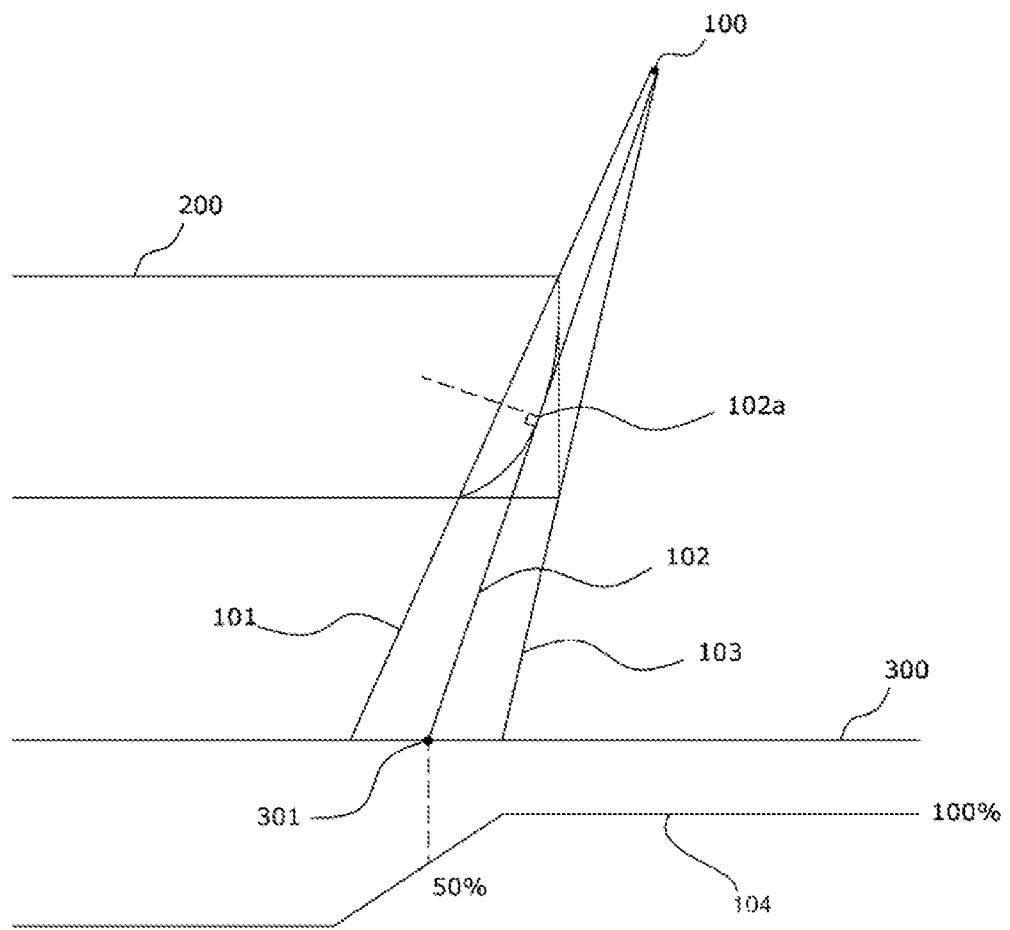
FIG. 6 is a view showing a method of forming edges of the collimator in the X-ray collimator and the X-ray imaging apparatus using the same according to an embodiment of the present invention.

FIG. 6 is a view showing a method of forming edges of the collimator 200 in the X-ray collimator and the X-ray imaging apparatus using the same according to an embodiment of the present invention.

Assuming that the opening of the collimator 200 is angled for convenience, the penumbra of the X-ray image occurs between a first X-ray path 103 where X-rays of the X-rays radially irradiated from the of the X-ray light source 100 penetrate through the angled edge at the minimum length, and a second X-ray path 101 having a minimum angle with the first X-ray path 103 of the completely blocked X-rays.

The opening of the collimator according to the present invention may be curved to have a predetermined curvature based on one point of the area of the above penumbra A where intensity 104 of the X-rays detected by the X-ray detector 300 is between about 40% and 60% of the initial intensity of the X-rays, and preferably, based on any one point of contact 102*a* tangent to a third X-ray path 102 reaching a point 301 where the intensity is 50%.

Here, although the radius of curvature and the point of contact 102*a* may be arbitrarily determined, it is preferred that the radius of curvature is equal to or less than a thickness of the collimator, more particularly, the shielding metal plate, and equal to or more than half of the thickness thereof. Further, the edge of the opening of the collimator may be continuously curved in a plurality of curvatures, and in this case, it is preferable that the curvature corresponding to the tangent is formed larger than the curvature corresponding to the periphery thereof.

According to the X-ray collimator and the X-ray imaging apparatus using the same according to an embodiment of the present invention configured as described above, it is possible to reduce the penumbra area of about 3 mm width for a 36 mm wide X-ray detector 300.

Meanwhile, as the penumbra is decreased, the quality of the image is increased, and the accuracy of the control by the driving unit 400 is also increased. Accordingly, the present invention can be effective when applied to X-ray images that require high-speed control of the X-rays FOV, especially scan type cephalometric images.

Although a preferred embodiment of the present invention has been described for illustrative purposes, those skilled in the art will appreciate that various modifications, additions and substitutions are possible, without departing from the scope and spirit of the invention as disclosed in the accompanying claims.

The invention claimed is:

1. An X-ray imaging apparatus comprising:
an X-ray light source configured to emit X-rays;
an X-ray detector configured to detect the X-rays; and
a collimator configured to provide an opening to determine an FOV of the X-rays between the X-ray light source and the X-ray detector,
wherein the opening is configured such that at least one of a first edge at an entrance side facing the X-ray light source and a second edge at an exit side facing the X-ray detector is formed in a curved shape, and
wherein the X-ray light source and the collimator are moved with respect to each other in a moving direction,
a first side edge of the opening is configured to be in a vertically angled shape at the first edge and in a curved shape at the second edge,
a second side edge facing the first side edge of the opening and is configured to be in the curved shape at both the first edge and the second edge, and
the first side edge goes before the second side edge in the moving direction.

2. The apparatus of claim 1, wherein the curved shape is an arc shape.

3. The apparatus of claim 1, wherein the curved shape is an arc tangent to a line which is virtually formed by connecting the X-ray light source and a predetermined point of the X-ray detector, wherein the predetermined point is where intensity of the X-rays detected by the X-ray detector becomes 40% or more and 60% or less, when both of the first edge and the second edge are in rectangular shape.

4. The apparatus of claim 3, wherein a radius of curvature of the arc is equal to or less than a thickness of the collimator and equal to or more than half of the thickness of the collimator.

5. An X-ray collimator configure to provide an opening to determine an FOV of X-rays between an X-ray light source configured to emit the X-rays and an X-ray detector configured to detect the X-rays,
wherein when the X-ray light source and the collimator are arranged in a fixed relative position, the opening includes a first edge facing the X-ray light source being in an angled shape and a second edge facing the X-ray detector being in a curved shape;
when the X-ray detector and the collimator are moved with respect to each other in one direction, a first side edge of the opening facing the moving direction is configured to be in an angled shape at the first edge and in a curved shape at the second edge, and a second side edge of the opening is configured to be in the curved shape at both the first edge and the second edge; and
when the X-ray detector and the collimator are moved with respect to each other in opposite directions, the opening includes the first edge and the second edge being in the curved shape.

6. The collimator of claim 5, wherein the curved shape is an arc shape.

7. The collimator of claim 5, wherein the curved shape is an arc tangent to a line which is virtually formed by connecting the X-ray light source and a predetermined point of the X-ray detector, wherein the predetermined point is where intensity of the X-rays detected by the X-ray detector becomes 40% or more and 60% or less when the first edge and the second edge are in a rectangular shape.

* * * * *